(12) United States Patent
Sitar

(10) Patent No.: US 6,309,606 B1
(45) Date of Patent: Oct. 30, 2001

(54) DEVICE AND METHOD FOR THE SEPARATION OF HUMAN OR ANIMAL CELLS OF DIFFERENT DENSITIES FROM CELLULAR DISPERSIONS WHICH CONTAIN THEM

(76) Inventor: Giammaria Sitar, Corso Partigiani, 32 27012, Certosa Di Pavia (Prov. of Pavia) (IT)

( * ) Notice: Subject to any disclaimer, the term of this patent is extended or adjusted under 35 U.S.C. 154(b) by 0 days.

(21) Appl. No.: 09/509,885
(22) PCT Filed: Oct. 29, 1998
(86) PCT No.: PCT/EP98/06865
§ 371 Date: Apr. 3, 2000
§ 102(e) Date: Apr. 3, 2000
(87) PCT Pub. No.: WO99/23471
PCT Pub. Date: May 14, 1999

(30) Foreign Application Priority Data

Oct. 31, 1997 (IT) .............................................. MI97A2457

(51) Int. Cl.$^7$ ...................................................... B01L 3/00
(52) U.S. Cl. .............................. 422/102; 494/26; 494/27; 494/37
(58) Field of Search ................................... 422/101, 102, 422/72; 210/781, 782; 494/16–18, 23, 37, 25–30, 42, 56, 65, 67, 85

(56) References Cited

U.S. PATENT DOCUMENTS

| | | | |
|---|---|---|---|
| 2,536,423 | * | 1/1951 | Cohen et al. . |
| 3,004,050 | * | 10/1961 | Ayres . |
| 3,513,976 | * | 5/1970 | James . |
| 4,146,172 | | 3/1979 | Cullis . |
| 5,100,372 | | 3/1992 | Headley . |
| 5,277,873 | * | 1/1994 | Hsei ..................................... 422/102 |
| 5,674,458 | * | 10/1997 | Holm ................................... 422/102 |

FOREIGN PATENT DOCUMENTS

| | | |
|---|---|---|
| 0198462 | 10/1986 | (EP) . |
| 0420153 | 4/1991 | (EP) . |
| 0475457 | 3/1992 | (EP) . |
| 0486480 | 5/1992 | (EP) . |
| 9607097 | 3/1996 | (WO) . |

OTHER PUBLICATIONS

Haematologica, Jan.–Feb. 1989, vol. 74, pp. 95–111, "Physical Procedures for the Separation of Blood and Marrow Cells", Sitar, G. et al.

International Journal of Analytical and Preparative Methods, 1981, vol. 117, pp. 354–365, "A Separation Chamber to Sort Cells, Nuclei, and Chromosomes at Moderate g forges", Tulp, A.

* cited by examiner

Primary Examiner—Charles E. Cooley

(57) ABSTRACT

A device and a method are provided to efficaciously and rapidly separate human or animal cells of different densities from the dispersions which contain them, the device comprising an elongated chamber containing at least a first channel, one end of which opens on the inside of the chamber near the base and a second channel whose end opens in the chamber at a level corresponding to the top of the device, and wherein there is at least a third additional channel, one end of which opens at an intermediate level of the chamber; and the method comprises introducing a dispersion of such cells into the chamber previously filled with a liquid with increasing density gradient, followed by centrifugation and by recovering the distinct fractions of cells with different densities through at least one hole situated at an intermediate level of the chamber length.

2 Claims, 2 Drawing Sheets

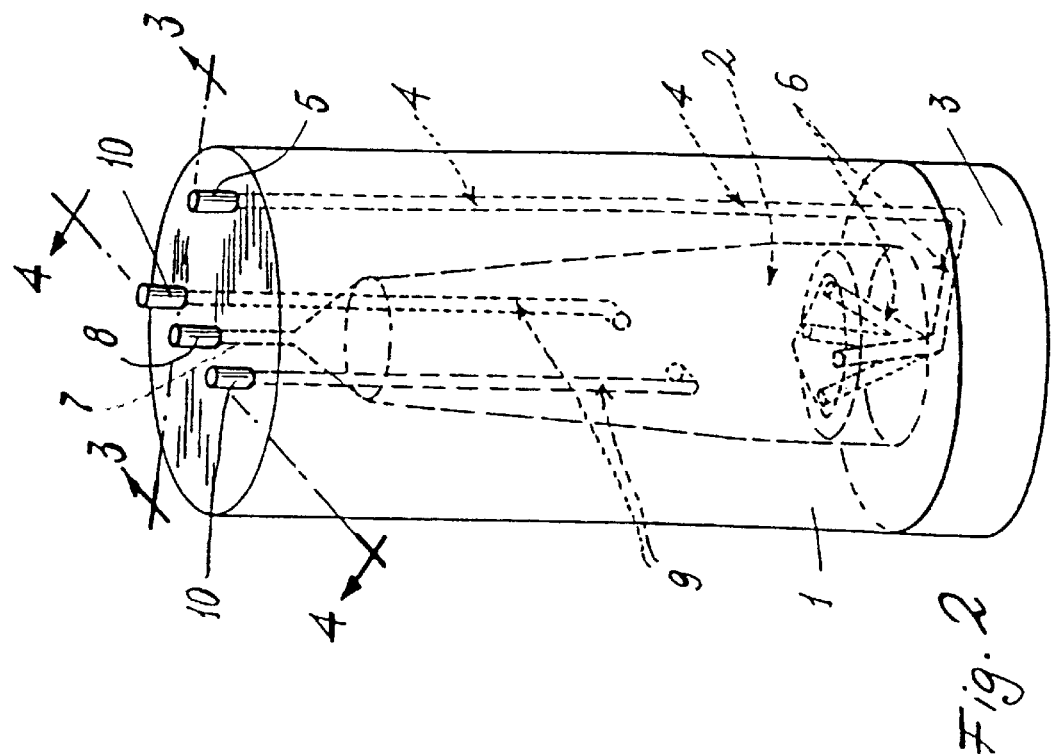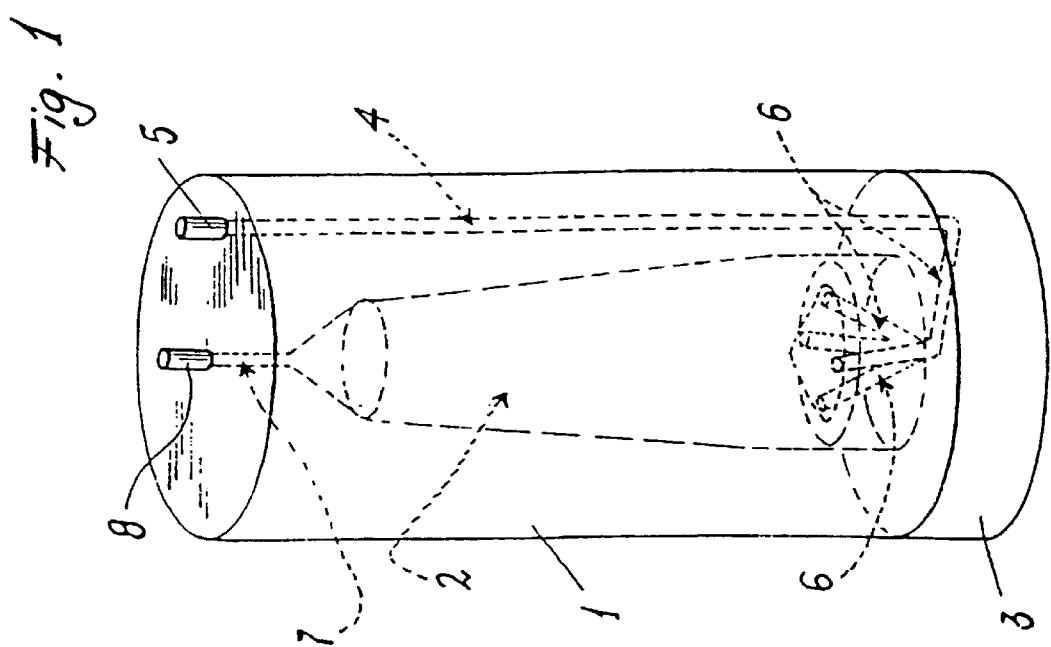

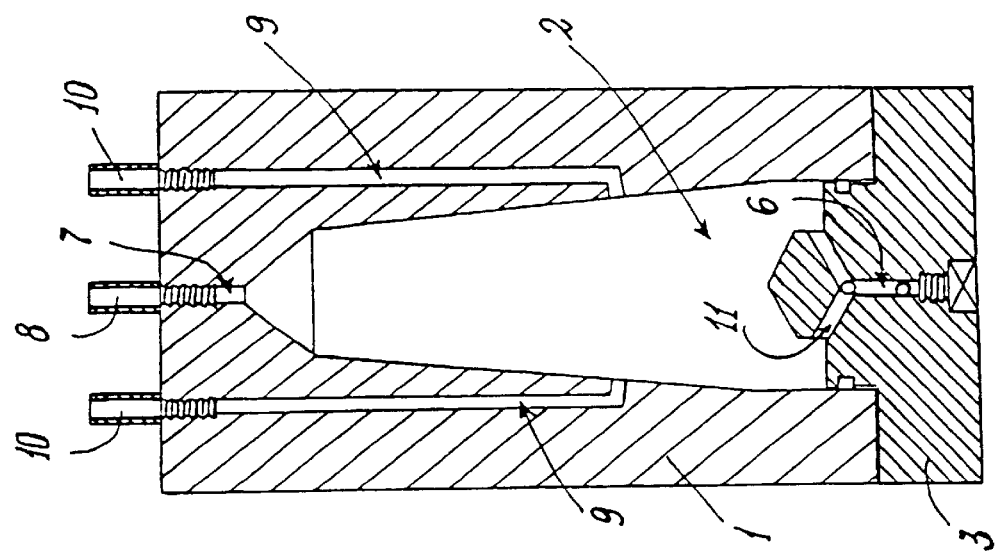
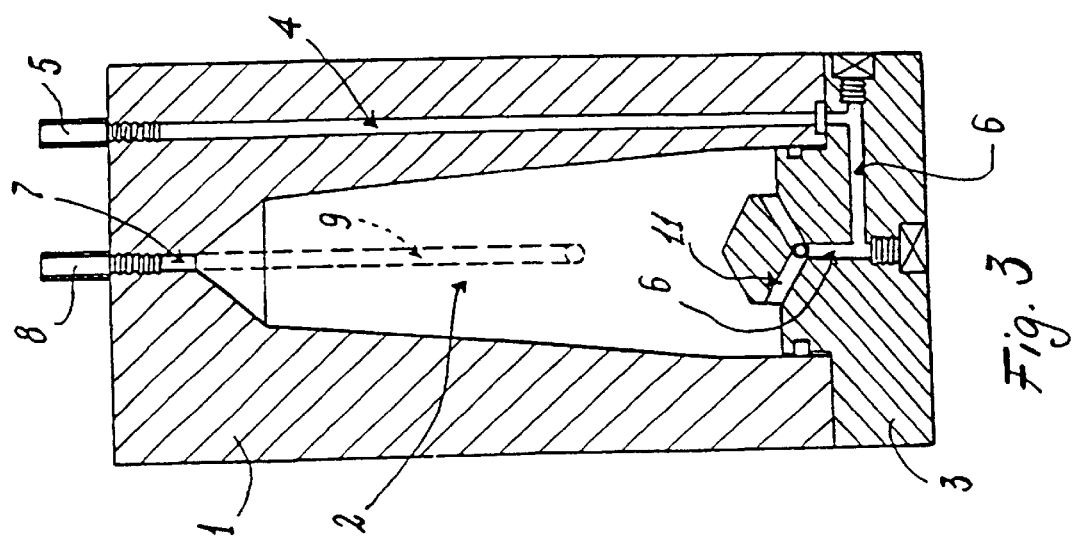

DEVICE AND METHOD FOR THE SEPARATION OF HUMAN OR ANIMAL CELLS OF DIFFERENT DENSITIES FROM CELLULAR DISPERSIONS WHICH CONTAIN THEM

SUMMARY

The invention concerns a device and a method which allow the efficacious and rapid separation of organic cellular populations of different densities, from the dispersions which contain them, said device comprising an elongated chamber whose cross section decreases from the base towards the top of the device and said method comprising the introduction of a dispersion of a cell population into said chamber of the device previously filled with a liquid whose density varies from a maximum, near the device base, to a minimum near the top, subjecting the device with the cellular dispersion to centrifugation and collecting the separated fractions by introducing a very dense water immiscible liquid at the base of the separator device while simultaneously pumping a gas at the same pressure as said very dense liquid, to the device top so that the layered cellular fractions inside the chamber are expelled through at least one hole situated at an intermediate level of said chamber length.

PRIOR ART

The invention refers to both a device and method for the separation of human or animal cellular fractions of different densities, from cell populations present in cellular dispersions.

It is known that human or animal cells have differing densities (generally between 1.04 g/cm3 and 1.1 g/cm3) and that each cell type has its own characteristic density.

It is also known that it is often important and necessary to separate differing cell types for possible concentration or purification of the same, from a dispersion of a heterogeneous population of cells. This is fundamental in making the biochemical and functional analyses possible on both normal cells and neoplastic populations.

The finer and more careful the separation of different density cells, and the more rapid is the separation operation then the data obtained will be equally good and useful, with consequent benefits to the practical procedure.

If one considers, for example, that certain types of cells are present in the blood or human tissues in extremely reduced quantities, it is evident that from their effective and rapid identification, the possibility of chemical, biochemical or medical intervention, otherwise impossible or only hypothetical, could follow.

The most advanced cell separation technique in current use employs a separator device consisting of a casing with an internal cavity. The latter is laterally delimited by tapered surfaces, with the greatest cross section near the end or base from which a tube or duct end is connectable to a peristaltic pump. The cavity is tapered towards the opposite end or top of the casing, which has an outlet hole. Initially, a liquid is introduced into the base cavity of the separator device using the peristaltic pump and a gradient mixer. The liquid density slowly increases as the quantity of liquid in the cavity increases, until filling it. Thus, the separator device cavity is filled with a liquid which is practically made up of successive and continuous strata of liquid, increasing in density from the top to the base of the device cavity. At this point, the liquid supply is suspended and a dispersion of the cellular population to be separated into homogeneous cellular fractions by density is introduced through the hole in the top, until the upper cavity section is filled: at the same time as the dispersion introduction, a corresponding volume of the liquid first introduced is drawn off from the separator device base, so that the cellular population dispersion can fall into the device cavity.

The separator device is then closed in a centrifuge, with the rotation axis perpendicular to the separator device axis and near its top, during centrifugation. In the centrifuge, a very large force is transmitted to the liquid closed in the device (for example 400 g), resulting in the distribution of the cellular population dispersion in the liquid in the form of cellular bands (or strata) of differing densities.

The separator device is then removed from the centrifuge and a very dense water immiscible liquid is introduced into the base causing the expulsion (from the hole in the top of the same device) of the fractionated cellular dispersion as described: the desired number (for example 10 or 12) of distinct dispersion fractions with an increasing density gradient are extracted through the separator device top, the cells present in each fraction having different densities to the adjacent fractions.

The device and the methodology briefly outlined above, are described in detail by Giammaria Sitar and Piermaria Fomasari in HAEMATOLOGICA, Vol. 74, N1, January–February 1989; and by Pretlow II TG and Pretlow TP eds. Cell Separation: method and selected applications, New York, Academic Press, 1982 (5 volumes).

The recovery system of the different separated cell fractions described above, has its limits, however, and presents some serious problems. Infact, the collecting of the different and subsequent cell fractions is carried out through a small hole in the separator device top, under the push of a dense liquid which is pumped in at the device base. This causes a hydrodynamic disturbance in the different adjoining strata where the cell density is different, and causes the widening (well known to field technicians) of the strata or bands where the different density cells are collected or distributed, resulting in the contraction of the liquid strata separating the bands where are collected the cells of mainly homogeneous density and different from band to band, which can even lead to the remixing of the various cellular fractions that were separated during centrifugation. This phenomenon is more serious and unacceptable, the narrower the bands, in which the cells have been collected, and the smaller the distance separating one cell from another.

In order to try and minimise these problems, the pressurised liquid at the base of the separator device is introduced with extreme slowness, a fact which leads, however, to long and unacceptable times necessary for the collection of the different cellular fractions. See the publications of Giammaria Sitar and Piermaria Fomasari already mentioned; and TULP, Anal. Biochem. 1981, vol. 117, pages 354–365.

DESCRIPTION OF THE INVENTION

The main aim of the present invention is that of finding a device and method which allow the easy and very clear collection of cellular fractions which have been separated in the device after centrifugation.

Another aim is that of allowing the recovery of the different cellular fractions in shorter times than is currently possible, making the collection of useful data possible, which would otherwise have proved useless.

The above aims, along with others, are satisfied with a separator device with a base and top, containing an elongated chamber, whose cross section decreases from the base towards the device top, the latter containing at least a first channel, one end of which opens onto the inside of the said chamber near the said base, the other end connectable to a pressurised liquid source and a second channel, one end of which opens into the same chamber corresponding to the device top, characterised by the fact that in the said device there is at least an additional channel, one end of which opens along the said chamber length, the other end opening onto the exterior of the device.

The invention also concerns the separation method of cellular fractions from dispersions of human or animal cell populations, in which, first of all, the dispersion of a cell population is introduced into the separator device chamber, previously filled with a liquid whose density varies from a maximum near the device base and a minimum near the top. The device is then subjected to centrifugation so as to distribute the cells into distinct fractions with differing densities, the method being characterised by the fact that the separated fraction recovery occurs by introducing, in the device base, a very dense, water immiscible liquid while simultaneously pumping a gas to the top (at the same delivery pressure as the very dense liquid), so that the layered cellular fractions inside the chamber are expelled through at least one hole situated in an intermediary zone along the said chamber length.

It was found, that proceeding in the above manner the cell bands, which were found layered in the separator device, were compressed after centrifugation (instead of expanding, as happens with the known method) in the same chamber, in a way that the various bands could be recovered separately in a clear manner, being expelled from the chamber (through the holes located laterally to the same chamber) without undergoing any hydrodynamic disturbance, i.e. there is no cell band remixing with those immediately adjacent.

It was also ascertained that, by proceeding in the manner described, the various cellular fractions could be separated and recovered at greater speeds than with the known technique, and cellular fractions are not mixed, as already mentioned. In order to make clearer both the device structure and the invention procedure, there will now follow the description of a potential application, as an unlimiting example, with reference to the enclosed figures.

BRIEF DESCRIPTION OF THE DRAWINGS

FIG. 1 is a schematic view of a known separator device of cells;

FIG. 2, represents, a schematic view of a separator device according to the invention of which:

FIGS. 3 and 4 are longitudinal sections of the device according to the lines 3—3 and respectively 4—4 of FIG. 2.

Reference is made, first of all, to FIG. 1 which illustrates a separator device of known structure made of an elongated casing 1 with an internal bell cavity 2 delimited by a substantially conical surface (dotted lines) with a greater cross section towards its base (with respect to the diagram) where there is the base 3 body affixed, which seal closes the cavity 2. Casing 1 is crossed by a duct 4 from whose upper end, a tube 5 extends, whose lower end opens inside cavity 2 through the channels 6 located in base 3 casing which is fixed to casing 1 in a suitable way, for example, with a series of bolts (not shown) or screw connection.

According to the present invention near the base of the device a flow deflector 11 is provided to disperse evenly the incoming fluid arriving from the channels 6, through the entire cross section of the inside chamber 2.

Cavity 2 is tapered towards the top of casing 1 which is crossed by a duct 7 linking the cavity with tube 8.

When one wishes to use the illustrated device, cavity 2 is filled, in the known way using tube 5, duct 4 and channels 6, with a liquid whose density gradually increases as it is introduced into the cavity, until filling it.

Thus cavity 2 is filled with a liquid which is practically made up of successive and continuous strata of liquid with increasing densities from the top to the base of the device. The liquid supply, through tube 5, is then stopped and the cellular population dispersion to be separated into homogeneous cellular fractions by density is introduced in cavity 2, while a corresponding volume of liquid is drawn off through tube 5.

The separator device is then placed in a centrifuge and the centrifugation proceeds at high speed until the distribution of the cellular population dispersion in the liquid, in the form of cellular strata of different densities, is obtained.

After the centrifugation step, a very dense water immiscible liquid is introduced into cavity 2, through tube 5, causing the expulsion of the cellular dispersion fractionated in the manner described from tube 8 collecting the desired number of distinct cellular dispersion fractions of increasing density gradient.

The recovery system of the different cell fractions described above with reference to FIG. 1, presents the serious problem that the expulsion of the differing cellular fractions by tube 8 occurs entirely with the push of the dense liquid coming out from channels 6 at the device base, with the consequent well known contraction or thinning of the liquid strata separating the bands where are collected the cells of homogeneous density but different from band to band, (resulting in difficulties of separate collection of the different bands). This can lead to serious and unacceptable remixing of the differing cellular fractions that were separated during centrifugation.

To minimise the above problem, the introduction of the liquid at the base of cavity 2 is carried out with extreme slowness, which means long times are necessary for the recovery of the different cellular fractions which is extremely serious as known to the field technicians.

FIGS. 2 to 4 illustrate a separator device according to the present invention.

This separator device is similar to that in FIG. 1: for clarity, the same reference numbers used in FIG. 1 have been adopted for FIGS. 2 to 4 to illustrate the various parts.

The separator device of FIGS. 2 to 4 is different from that of FIG. 1 for the fact that two supplementary ducts 9, are located in casing 1 (in reality, there could be more than two, or even one) from which a tube 10 extends from the upper end, whose lower end opens into the inside of cavity 2 halfway along its length.

Moreover, near the base of the device a flow deflector 11 may be provided to disperse evenly the incoming fluid arriving from the channels 6, through the entire cross section of the inside chamber 2.

The filling and centrifugation procedures of the device in FIGS. 2 to 4 have already been described with reference to FIG. 1 and will not therefore be repeated here. The recovery stage of the different separated cellular fractions from the device is very different.

In fact, the collection of the separated fractions, which occurs after centrifugation, is carried out by introducing a very dense water immiscible liquid at the base of cavity 2 (as in the known technique) while simultaneously pumping a gas (for example, air) through tube 8 to the top at the same pressure as the dense liquid, so that the layered cellular fractions inside cavity 2 are compressed and forced out through ducts 9.

It was found, proceeding in the above manner, that not only the recovery of the different cell bands which were layered in cavity 2, is performed at a much higher velocity than was possible with the known technique, but also happens so that the bands are compressed in cavity 2 (instead of expanding, as in the known technique) and can therefore be collected separately in a clear manner, being expelled to the exterior of cavity 2 without undergoing any hydrodynamic disturbance, i.e. without cell band remixing with those immediately adjacent, thus allowing a clear and rapid individuation of cells of differing densities initially present in the cell population examined.

order to illustrate the use of the device, according to the present invention, the separation of cellular populations from human bone marrow will be taken as an example.

It is known that human bone marrow contains various cellular populations with differing densities (see "Haematologica", January–February 1997): some cellular types are light (low density), others are of intermediate density and others are heavy (high density). In order to separate said cellular populations and collect them separately, a cellular separator is used as described above with reference to FIGS. 2 to 4, in which cavity 2 has a volume of 90 ml, and the various ducts are 2 mm in diameter.

90 ml of liquid (with a continuous density gradient between 1.050 and 1.100 g/l) is introduced into the separator device through duct 4. Then 5 ml of bone marrow monodispersed cellular suspension is introduced above the liquid already present through channel 8.

The cellular separator device, thus loaded, is then centrifuged at 400 g for 1 hour, to obtain successive stratification of the different cellular populations in discrete bands of the suspension present inside cavity 2 of the device. After centrifugation, a heavy water immiscible liquid is introduced at the base through duct 4 at a flow velocity of 2 ml/min, while simultaneously pumping air from the top, through tube 8, at the same rate (2 ml/min). Thus the cellular fraction of intermediate density, present at the height of the duct 9 exit holes located halfway in cavity 2, is compressed and forced out through these and is collected in a few minutes (approximately 5 minutes), without remixing with the other cellular fractions due to hydrodynamic disturbances.

Similarly, to collect the light cellular fractions situated in the upper part of the suspension, or the heavy ones placed in the lower part of the same suspension, it is sufficient to move the strata of differing densities towards the top or the bottom (using the peristaltic pump connected to ducts 4 and tube 8) so as to obtain the cellular fraction desired, at the height of the lateral exit holes (ducts 9) after which, in cavity 2, heavy liquid is introduced from the base (using the peristaltic pump) and air from the top to collect the desired cellular fraction through the lateral exit holes mentioned.

What is claimed is:

1. A device for the separation of human or animal cells of different densities, from cellular dispersions in which they are contained, having a base and a top and containing an elongated chamber whose cross section decreases from the base towards the top of the device which contains at least a first channel, one end of which opens on the inside of the chamber near the base and the other end connectable to a pressurized liquid source and a second channel whose end opens in the chamber at a level corresponding to the device top, wherein there is at least a third channel in the device, one end of which opens at an intermediate level of the chamber length, and the other end opens outwards from the device and wherein near the base a flow deflector is provided to disperse evenly through the entire cross section of the inside chamber of the incoming fluid arriving from the first channel.

2. A separation method of human or animal cells of different densities from cellular dispersions which contain them comprising using the device according to claim 1, wherein a dispersion of a cell population is introduced into the chamber of the device previously filled with a liquid whose density varies from a maximum near the device base, to a minimum near the top, the device with cellular dispersion is subjected to centrifugation for the distribution of the cells into distinct fractions with differing densities, and after the centrifugation step the recovery of the distinct fractions takes place by introducing a very dense water immiscible liquid at the base of the device while simultaneously pumping a gas, at the same pressure an the very dense liquid, to the device top so that the layered cellular fractions inside the chamber are compressed and forced out through at least one hole situated at an intermediate level of the chamber length.

* * * * *